US008993283B2

(12) United States Patent
Matsuura et al.

(10) Patent No.: US 8,993,283 B2
(45) Date of Patent: Mar. 31, 2015

(54) PRODUCTION METHOD FOR BIOMASS ALCOHOL

(75) Inventors: Kazuo Matsuura, Naruto (JP); Fusatsugu Abe, Naruto (JP); Tetsuo Fukazu, Otsu (JP); Takuji Cho, Tokyo (JP); Kousuke Kimoto, Tokyo (JP)

(73) Assignees: Ultrasound Brewery, Tokushima (JP); Mitsui Engineering & Shipbuilding Co., Ltd., Tokyo (JP)

( * ) Notice: Subject to any disclaimer, the term of this patent is extended or adjusted under 35 U.S.C. 154(b) by 766 days.

(21) Appl. No.: 12/935,499

(22) PCT Filed: Mar. 31, 2009

(86) PCT No.: PCT/JP2009/001500
§ 371 (c)(1),
(2), (4) Date: Nov. 8, 2010

(87) PCT Pub. No.: WO2009/122728
PCT Pub. Date: Oct. 8, 2009

(65) Prior Publication Data
US 2011/0053234 A1 Mar. 3, 2011

(30) Foreign Application Priority Data

Mar. 31, 2008 (JP) ................................. 2008-091616

(51) Int. Cl.
| C12P 7/02 | (2006.01) |
| C12P 7/06 | (2006.01) |
| C12P 7/10 | (2006.01) |
| C07B 63/00 | (2006.01) |
| B05B 17/06 | (2006.01) |

(52) U.S. Cl.
CPC .............. *C12P 7/10* (2013.01); *B05B 17/0615* (2013.01); *Y02E 50/16* (2013.01); *Y02E 50/17* (2013.01)
USPC ........ 435/155; 435/161; 435/165; 204/158.21

(58) Field of Classification Search
USPC ....................... 435/155, 161; 536/52; 585/242
See application file for complete search history.

(56) References Cited

U.S. PATENT DOCUMENTS

| 3,675,442 | A | * | 7/1972 | Swanson | 62/285 |
| 4,276,124 | A | * | 6/1981 | Mock | 202/236 |
| 4,316,956 | A | * | 2/1982 | Lutzen | 435/96 |
| 4,321,328 | A | * | 3/1982 | Hoge | 435/165 |
| 4,428,967 | A | * | 1/1984 | Goering et al. | 426/28 |
| 4,617,270 | A | * | 10/1986 | Anderson et al. | 435/161 |
| 5,290,403 | A | * | 3/1994 | Saask | 202/182 |
| 5,424,417 | A | * | 6/1995 | Torget et al. | 536/56 |
| 6,919,000 | B2 | * | 7/2005 | Klausner et al. | 203/10 |
| 7,103,992 | B2 | * | 9/2006 | Duden et al. | 34/381 |
| 7,504,026 | B2 | | 3/2009 | Matsuura et al. | |
| 2005/0223890 | A1 | * | 10/2005 | Matsuura | 95/29 |
| 2007/0031953 | A1 | * | 2/2007 | Dunson et al. | 435/161 |
| 2007/0190626 | A1 | * | 8/2007 | Wilkening et al. | 435/161 |
| 2007/0193874 | A1 | * | 8/2007 | Adiga et al. | 203/99 |
| 2007/0295595 | A1 | * | 12/2007 | Matsuura | 204/158.2 |
| 2008/0017560 | A1 | * | 1/2008 | Matsuura et al. | 210/151 |
| 2008/0064906 | A1 | * | 3/2008 | Foody et al. | 585/242 |

FOREIGN PATENT DOCUMENTS

| EP | 1 875 951 A2 | 1/2008 |
| JP | 2001-262162 A | 9/2001 |
| JP | 2003-311102 A | 11/2003 |
| JP | 3789845 B2 | 6/2006 |
| JP | 2007-202517 A | 8/2007 |
| JP | 2008-30026 A | 2/2008 |
| JP | 2008-49220 A | 3/2008 |
| WO | WO 2008030262 | * 3/2008 |
| WO | WO 2008076717 | * 6/2008 |

OTHER PUBLICATIONS

Wet-scrubbers, 2013.*
Cyclone-separator, 2013.*
S.Nii, A novel method to separate organic compounds using ultrasonic atomization, Trans IChemE, May 2006.*
International Search Report dated Jun. 23, 2009 in International Application No. PCT/JP2009/001500.
Kazuo Matsuura, "Journal of Japanese Society of Food Engineering", Dec. 9, 2008, vol. 28 No. 3, pp. 27-29.

* cited by examiner

*Primary Examiner* — Taeyoon Kim
*Assistant Examiner* — Srikanth Patury
(74) *Attorney, Agent, or Firm* — Birch, Stewart, Kolasch & Birch, LLP

(57) ABSTRACT

A production method for biomass-alcohol includes a saccharification step of saccharifying biomass, a first concentrating step of ultrasonically vibrating the saccharified solution and atomizing the saccharified solution into a mist, so as to elevate the sugar concentration in the saccharified solution by removing water from the saccharified solution, a fermentation step of fermenting the saccharified solution concentrated in the first concentrating step to form an alcohol water solution, and second concentrating step of separating alcohol from the alcohol water solution fermented in the fermentation step.

15 Claims, 6 Drawing Sheets

PRODUCTION METHOD FOR BIOMASS ALCOHOL

BACKGROUND OF THE INVENTION

1. Field of the Invention

This invention relates to a production method for biomass alcohol fermented and purified from plants including polysaccharide or animals.

2. Description of the Related Art

A production method for alcohol from sugar cane which is one of biomass is in practical. This method for alcohol production includes two steps, cane juice is fermented to alcoholic solution, and the solution is distilled to higher alcohol content. In this method, bagasse is utilized as fuel to distill from fermented alcohol water solution to higher alcohol content. In this method, as bagasse is utilized as fuel, alcohol is efficiently manufactured. However, in this method, the amount of alcohol obtained from a unit cane is little because polysaccharide in whole cane can not be converted to alcohol by ordinal method.

The above mentioned problem can be solved by followed method. That is, biomass is crushed with water, the polysaccharide in biomass is converted to saccharified solution, and alcohol solution is fermented from saccharified solution and purified. See JP2007-202517 A and JP2001-262162 A. By this method, people can obtain several times of alcohol comparing the production method from only cane juice. By utilize this method, waste wood materials can be converted to alcohol. This method has two steps, biomass such as wood materials is crushed with large water, and polysaccharide in the water and crushed wood mixture is saccharified. Therefore, obtained saccharified solution contains much water. Saccharified solution with much water requires ambitious equipment and huge energy in the steps of alcohol fermentation and distillation. Additionally, huge water will be required in manufacturing.

SUMMARY OF THE INVENTION

The object of the invention is to solve the above mentioned problem, and to provide a production method for biomass alcohol that wood biomass such as materials and cane can be efficiently fermented, alcohol can be efficiently purified from fermented alcoholic aqueous solution, and simultaneously both equipment cost and running cost will be decreased.

The production method for biomass alcohol in this invention presents following method for biomass alcohol production.

The production method for biomass-alcohol includes a saccharification step of saccharifying biomass to produce a saccharified solution, a first concentrating step of ultrasonically vibrating the saccharified solution and atomizing the saccharified solution into a mist so as to elevate the sugar concentration in the saccharified solution by collecting the atomized mist and removing water from the saccharified solution, a fermentation step of fermenting the saccharified solution concentrated in the first concentrating step to form an alcohol water solution, and a second concentrating step of separating alcohol from the alcohol water solution fermented in the fermentation step.

In the production method for biomass-alcohol according to the invention, the water separated from the saccharified solution in the first concentrating step can be utilized for biomass saccharification in the saccharification spep.

In the production method for biomass-alcohol according to the invention, mist atomized by ultrasonic vibration can be separated by a cyclone, and a downward flux separated in the cyclone can be circulated to the saccharified solution.

In the production method for biomass-alcohol according to the invention, the mist atomized by ultrasonic vibration in the first concentrating step can be separated by a cyclone, an upward flux separated in the cyclone can be liquefied by bubbling in water bulk, and the liquefied water can be utilized for saccharification of biomass in the saccharification step.

In the production method for biomass-alcohol according to the invention, the saccharification step includes a first saccharification step of saccharifying hemicellulose in biomass by acid, and second saccharification step of saccharifying cellulose in biomass by enzyme.

In the production method for biomass-alcohol according to the invention, a surfactant can be added to saccharified solution of biomass and atomized into mist in the first concentrating step.

In the production method for biomass-alcohol according to the invention, mist can be collected under lower pressure condition than atmospheric pressure in the first concentrating step.

In the production method for biomass-alcohol according to the invention, the atomized mist can be carried by carrier gas containing hydrogen or helium or methane and collected in the first concentrating step.

In the production method for biomass-alcohol according to the invention, the saccharified solution heated in the saccharification step can be atomized into mist in the first concentrating step.

In the production method for biomass-alcohol according to the invention, the saccharification step is containing first saccharification step by acid and second saccharification step by enzyme under lower temperature than temperature of first saccharification step, thermal energy can be recovered through cooling saccharified solution at first saccharification step, simultaneously carrier gas at first concentrating step can be heated by the recovered thermal energy, and the saccharified solution can be ultrasonically atomized mist into carrier gas heated by the recovered energy.

The production method for biomass-alcohol according to the presented invention can efficiently purify alcohol, and can decrease both equipment cost and running cost, collecting alcohol from alcohol water solution fermented efficiently from biomass such as wood materials and cane. Because the production method in the present invention produces biomass-alcohol by saccharification step to saccharify biomass, first concentrating step of ultrasonically vibrating the saccharified solution and atomizing the saccharified solution into mist so as to elevate the sugar concentration in the saccharified solution by collecting the atomized mist and removing water from the saccharified solution, fermentation step of fermenting the saccharified solution concentrated in the first concentrating step, and second concentrating step of separating alcohol from the alcohol water solution fermented in the fermentation step. Particularly, the production method in the present invention saccharifies biomass polysaccharide to saccharified solution by hydrolysis, atomizes the solution into mist by ultrasonic vibration in the first concentrating step, elevates the sugar concentration by collecting the atomized mist and removing water from the saccharified solution, purifies alcohol from the dilute alcohol water solution fermented from the saccharified and concentrated solution. That is, the saccharified solution obtained in saccharification step is concentrated by atomizing the saccharified solution into mist by ultrasonic vibration and separating water from the saccharified solution. Ultrasonic vibration can separate water from the saccharified solution by using a property that water is atomized into mist more easily than sugar. The saccharified solution concentrated by separating water reaches higher alcohol concentration, so both the equipment cost and the running cost to purify alcohol can be decreased while high yield of alcohol from biomass is achieved. Moreover, the production method in the present invention can efficiently utilize the water by adding the water separated from the saccharified solution to biomass saccharification step.

The production method for biomass-alcohol according to the present invention can efficiently utilize the water separated from the concentrating step to reuse for saccharification of biomass in the saccharification step, whereby the water separated from the saccharified solution is utilized for biomass saccharification in the first concentrating step. This method can reduce the water cost for saccharification step in spite of efficiently using much water for biomass saccharification.

The production method for biomass-alcohol according to the present invention can efficiently utilize the collected sugar in atomized mist, whereby mist atomized by ultrasonic vibration is separated by a cyclone, downward flux separated in the cyclone is circulated to saccharified solution.

The production method for biomass-alcohol according to the present invention can efficiently utilize the separated water containing sugar for the saccharification step by collecting sugar in upward flux from a cyclone, whereby mist atomized by ultrasonic vibration is separated by the cyclone, upward flux separated in the cyclone is liquefied by bubbling in water bulk, the liquefied water is utilized for saccharification of biomass at saccharification step in the first concentrating step.

The production method for biomass-alcohol according to the present invention can efficiently saccharify the cellulose and hemicellulose in biomass, and can purify alcohol, whereby the saccharification step includes a first saccharification step of saccharifying hemicellulose in biomass by acid and a second saccharification step of saccharifying cellulose in biomass by enzyme.

The production method for biomass-alcohol according to the present invention can efficiently atomize the saccharified solution added surfactant into mist, can efficiently concentrate the saccharified solution in the first concentrating step, whereby a surfactant is added to saccharified solution of biomass and atomized into mist in the first concentrating step.

The production method for biomass-alcohol according to the present invention can efficiently collect, and can efficiently concentrate, whereby mist is collected under lower pressure condition than atmospheric pressure in the first concentrating step.

The production method for biomass-alcohol according to the present invention can efficiently atomize the mist using lighter molecular gas instead of air, whereby atomized mist is carried by carrier gas containing hydrogen or helium or methane and collected in the first concentrating step.

The production method for biomass-alcohol according to the present invention can efficiently atomize the saccharified and heated solution into mist by ultrasonic vibration in the first concentrating step, and can efficiently concentrate the saccharified solution in the first concentrating step.

The production method for biomass-alcohol according to the present invention can efficiently atomize the saccharified solution into mist by the waste heat generated in the first saccharification step and second saccharification step, whereby the carrier gas is heated by waste heat in the first saccharification step and second saccharification step. According to this method, the saccharified solution can be efficiently atomized with the waste heat effectively, because the waste heat generated in the saccharification step is usefully utilized for heating the carrier gas.

DETAILED DESCRIPTION OF THE EMBODIMENTS

Figure 1:
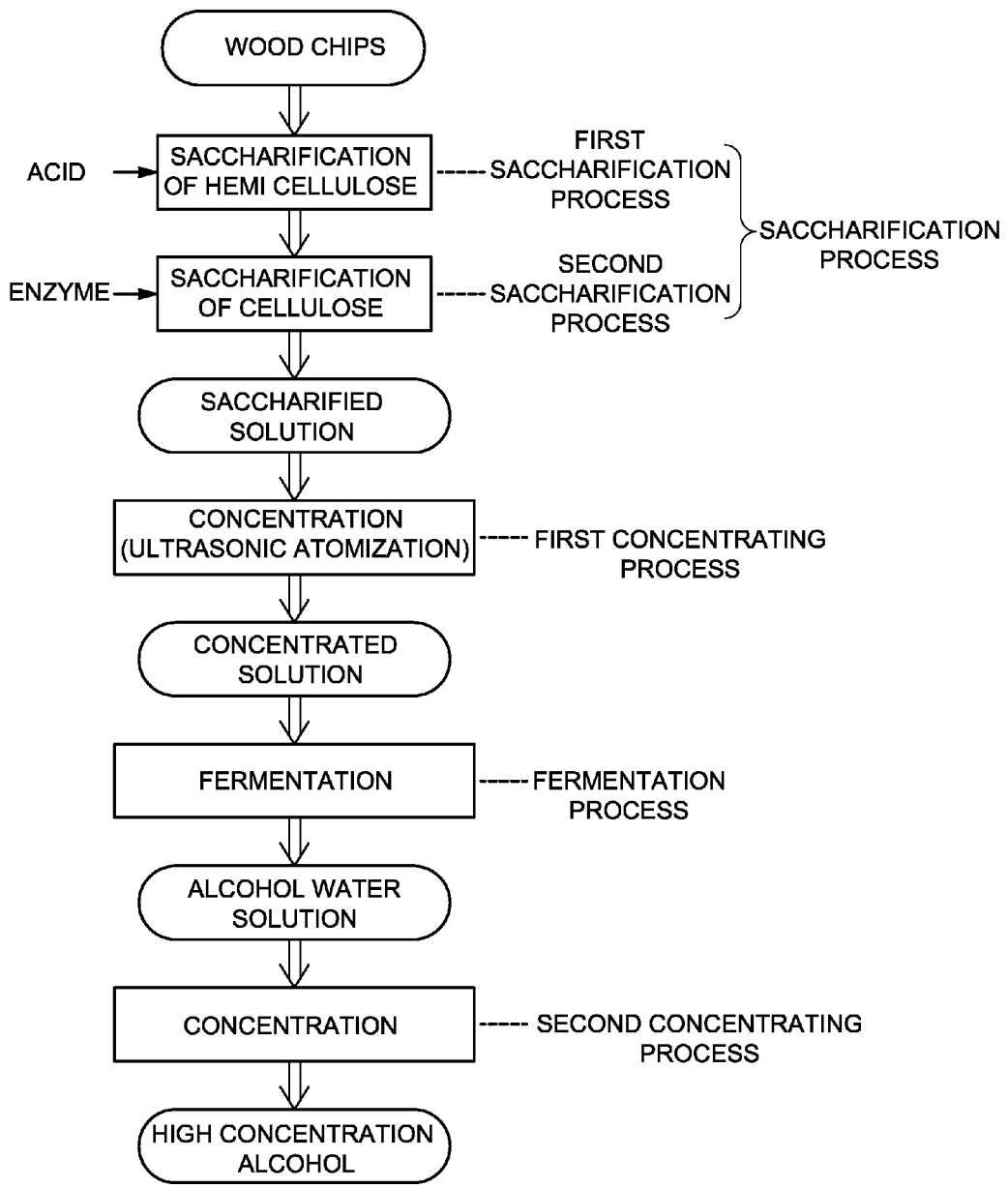
FIG. 1 is a process outline showing production method for biomass-alcohol according to an example of the present invention.

There is detail description for this invention based on the figures as follows. However, the following description just explains for the manufacturing methods of biomass alcohol to be embodied the technological ideas, this invention is not restricted by only following methods and conditions for the manufacturing methods of biomass alcohol.

Moreover, this disclosure is numbering to elements shown in this embodiment for understandings of the invention claims, the reference numerals are indicated with the elements shown in the figures and embodiment. However, the elements defined on the claims are not restricted by the elements in the embodiment.

Figure 2:
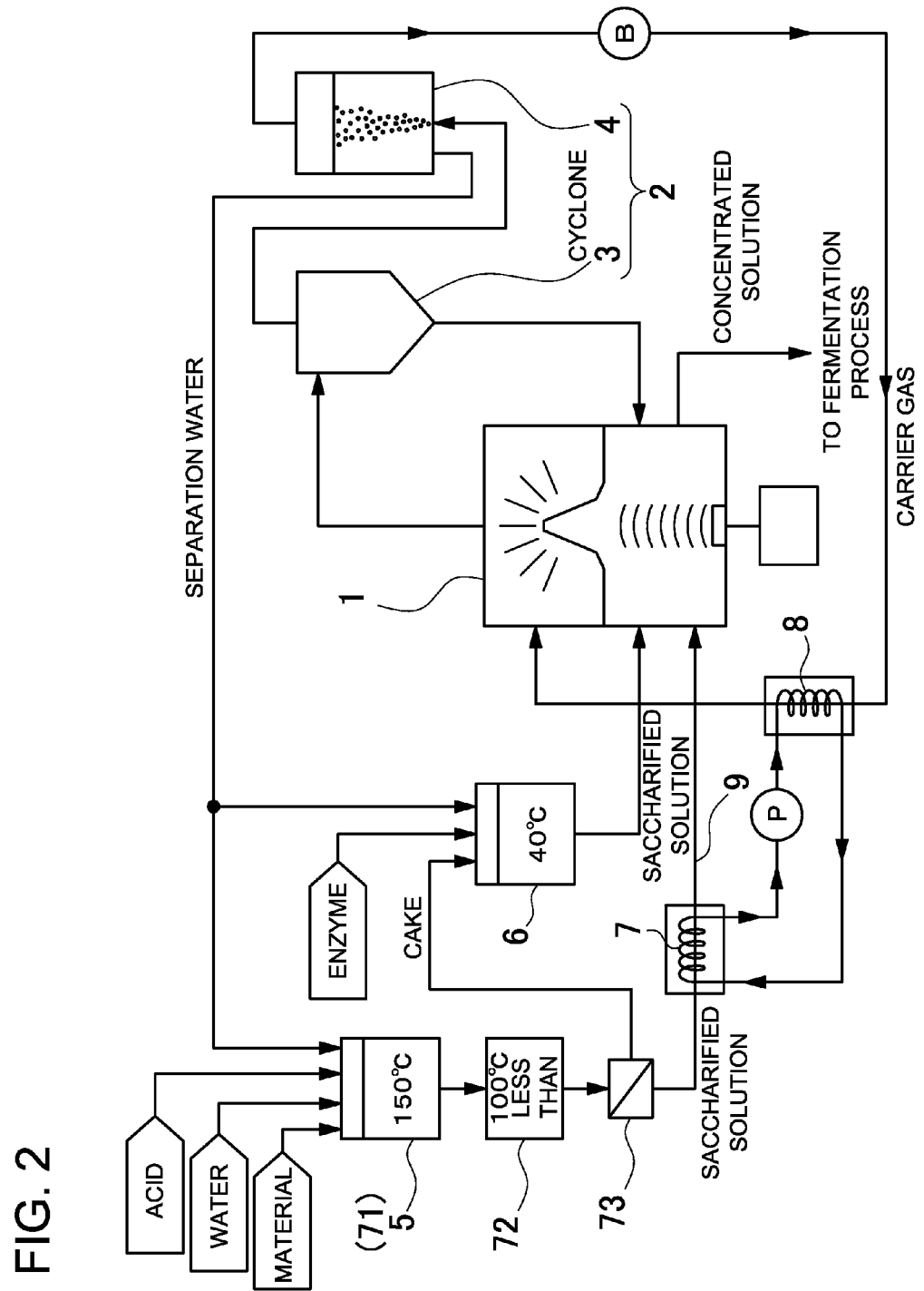
FIG. 2 is a schematic view showing a concentrating device for the saccharification step and the first concentrating step in the production method for biomass-alcohol according to an example of the present invention.

The production method for biomass-alcohol mentioned in this invention includes a saccharification step of saccharifying biomass, first concentrating step of ultrasonically vibrating the saccharified solution and atomizing the saccharified solution into mist, and to elevate the sugar concentration in the saccharified solution by collecting the atomized mist and removing water from the saccharified solution, fermentation step of fermenting the saccharified solution concentrated in the first concentrating step, and second concentrating step of separating alcohol from the alcohol water solution fermented in the fermentation step, as shown in the process outline of FIG. 1. FIG. 2 shows a schematic view of a concentrating device for the saccharification step and the first concentrating step.

In the production method for biomass-alcohol mentioned in this invention, the crushed wood chips are used as biomass. As the wood chips, waste wood made from broken buildings and lumber from thinning are crushed into small chips, for example, smaller than 3 cm. However, the present invention is not limited to wood materials as biomass. As biomass, all biomass containing polysaccaharide such as cane, corn, wheat, seaweed, and organic waste can be used. Wood material chips as biomass is saccharified through hydrolysis of polysaccharide by adding water in saccharification step.

The saccharification step includes two steps. The first step performs saccharification of hemicellulose in wood materials chips. The second step performs saccharification of cellulose after the completion of the first saccharification step, as shown in FIG. 1. As the first saccharification step, either the hydrolysis by acid or the hydrolysis by alkali is available. In the hydrolysis by acid, inorganic acids such as sulfuric acid, hydrochloric acid, nitrate is available, sulfuric acid is preferable. In the saccharification step of wood material chips by acid, the wood chips are immersed in dilute sulfuric acid, and then, hemicellulose is heated and saccharified at 140° C. to 200° C. In this first saccharification step, as shown in FIG. 2, the wood chips immersed in dilute sulfuric acid solution are saccharified through hemicellulose hydrolysis under high temperature, for example 150° C., and high pressure in a reactor 71 as a first tank 5. Saccharified slurry saccharified in the first saccharification step is cooled until less than 100° C. while the pressure in a decompression chamber 72 is reduced to atmospheric pressure in, then, the saccharified slurry is solid-liquid separated to saccharified solution and cake by a solid-liquid separator 73. The saccharified solution separated by solid-liquid separator is transferred to the first saccharification step. The solid content, cake separated by the solid-liquid separator 73 is transferred to the second saccharified step, and then saccharified by enzyme. In the second saccharification step, cellulose is enzymatically saccharified. The temperature condition in enzymatic saccharification step is lower than that in acid saccharification step. In this second saccharification step, after the addition of water to cake separated by the solid-liquid separator 73, enzyme is added, preferable temperature for enzyme is adjusted to, for example 40° C., cellulose is saccharified. The saccharified solution obtained in the second saccharification step is transferred to the first concentrating step.

While the saccharified solution separated by the solid-liquid separator 73 is transferred to the first concentrating step, thermal energy can be recovered by cooling the saccharified solution. The concentrating device in FIG. 2 has a cooling heat exchanger 7 on the way of a transfer tube 9 connected to the atomization chamber 1, the transfer tube 9 transfer the saccharified solution obtained in the first saccharification step to the atomization chamber 1, the saccharified solution obtained in the first concentrating step is cooled by the cooling heat exchanger 7, whereby thermal energy is recovered. The recovered thermal energy is utilized for heating the carrier gas for the next performance of the first concentrating step. The saccharified solution is ultrasonically atomized into the carrier gas heated by this recovered thermal energy, whereby the efficiency to atomize mist is increased. The recovered thermal energy is also utilized for heating the carrier gas for the second concentrating step. In the concentrating device in FIG. 2, the cooling heat exchanger 7 is connected onto the heating heat exchanger 8 to heat the carrier gas. The coolant is circulated between the cooling heat exchanger 7 and the heating heat exchanger 8. The coolant is heated by absorbing the thermal energy at the cooling heat exchanger 7, whereby the absorbed thermal energy is radiated at the heating heat exchanger 8 and heats the carrier gas. For example, water or oil is used as the coolant. This coolant is heated by absorbing the thermal energy from the saccharified solution obtained in the first saccharification step, and then, ejected from the cooling heat exchanger 7. For example, the coolant is ejected from the cooling heat exchanger at 45° C. The heated coolant ejected from the cooling heat exchanger 7 heats the carrier gas to generate mist at the heating heat exchanger 8. The carrier gas is heated by the heating heat exchanger 8 and supplied to the atomization chamber 1. The temperature of the coolant after the heat exchange with the carrier gas decreases. After temperature of the coolant decreased, the coolant is circulated from the heating heat exchanger 8 to the cooling heat exchanger 7, cools the cooling heat exchanger, and cools again the saccharified solution obtained in the first saccharification step. That is, the coolant absorbs the thermal energy from the saccharified solution obtained in the first saccharification step, whereby the absorbed thermal energy heats the carrier gas. The heating heat exchanger heats the carrier gas up to 25-30° C. However, the heating heat exchanger 8 can be also used for heating the carrier gas up to 14-40° C., and the heated carrier gas is supplied to the atomization chamber 1.

The coolant can also cool the cooling heat exchanger by own vaporization heat, and can also heat the heating heat exchanger by own condensation heat. In the cooling mechanism for cooling or heating the heat exchanger by vaporization heat or condensation heat of coolant, as shown in FIG. 3, the coolant is compressed by the compressor 46. The coolant compressed by the compressor 46 is supplied to the heating heat exchanger 8. The heating heat exchanger 8 cools the coolant, while the heat of coolant is radiated and liquefied. Therefore, the heating heat exchanger 8 is heated by the condensation heat of coolant. The liquefied coolant is transferred to the cooling heat exchanger 7 via an expansion valve 47. The expansion valve 47 expand the coolant through adiabatic expansion, the coolant is vaporized in inside of the cooling heat exchanger. Therefore, the cooling heat exchanger 7 is cooled by vaporization heat of coolant. The cooled coolant is inhaled into the compressor 46, and circulated to the heating heat exchanger. This cooling mechanism can raise the temperature in the heating heat exchanger 8 while the temperature in the cooling heat exchanger 7 is decreased. Therefore, in the first concentrating step, the temperature in the carrier gas supplied to the atomization chamber 1 can be raised.

The saccharified solution obtained in the saccharification step is not immediately fermented in the fermentation step. After the saccharified solution obtained in the saccharification step is concentrated in the first concentrating step, the saccharified solution is processed in alcoholic fermentation, as shown in FIG. 1. In the first concentrating step, the saccharified solution obtained in the first saccharification step is ultrasonically atomized into mist, whereby the water content is removed. The saccharified solution concentrated in the first concentrating step is fermented to alcohol water solution in the fermentation step. After that, the alcohol water solution is purified to higher alcohol content by concentrating in the second concentrating step. The present invention has a property that the saccharified solution is concentrated with ultrasonic vibration, the concentrated saccharified solution is fermented to alcohol, and the alcohol is purified. Therefore, the present invention does not restrict the method to saccharify biomass, as the method to saccharify by water addition, people can utilize all method already practically used or all method that will be developed in the future. Moreover, the present invention is not restricted only the following method described below that the saccharified solution concentrated in the first concentrating step is fermented to alcohol water solution, and the alcohol water solution is purified to higher alcohol content.

In the first concentrating step of concentrating the saccharified solution, the saccharified solution is ultrasonically atomized into mist, and the atomized mist is transferred to the collection portion with carrier gas, and concentrated. As the carrier gas to transfer the atomized mist, carrier gas containing one of hydrogen, helium, methane is available. As the carrier gas, inert gas is also available. Moreover, in the first concentrating step, surfactant can be added to the saccharified solution of biomass. The saccharified solution added surfactant is ultrasonically atomized into mist, efficiently.

In the first concentrating step, for example, 5% of the saccharified solution is concentrated to 10% by separation of water. The concentrating device in FIG. 2 includes the atomization chamber 1 to ultrasonically atomize the saccharified solution into mist and the collection portion 2 to collect the atomized mist. The atomization chamber 1 ultrasonically atomizes the saccharified solution into the mist, and transfers the atomized mist to the collection portion 2 with the carrier gas. The collection portion 2 includes the cyclone 3 and the water tank 4. In the first concentrating step, the collection portion 2 collects the mist under reduced pressure, preferably.

In the cyclone 3 of the collection portion 2 is used to rotate the carrier gas by centrifugation. The larger diameter mist is going downward along the inner wall of the cyclone and ejected from lower end as downward flux. The smaller diameter mist and gas are given smaller centrifugal force, ejected from center of the cyclone as upward flux. Comparing water and sugar, water has a smaller molecular weight than sugar, such that water is vaporized more easily than sugar. By that reason, in the case that the saccharified solution is ultrasonically atomized into the mist, water is more easily atomized into mist than sugar, the atomized mist is containing lower sugar concentration, on the other words, the water concentration is higher. Therefore, according to the saccharified solution is ultrasonically atomized into the mist, the saccharified solution can be separated and concentrated. Moreover, water content in the mist atomized from the saccharified solution is not 100%, containing little sugar concentration. The mist containing little sugar is separated the upward flux and the downward flux by the cyclone 3. Since the smaller mist and the vaporized component are ejected as the upward flux, the upward flux is containing more water easier to be vaporized than sugar, on the other hand, since the downward flux is from the larger diameter mist, the downward flux is containing more sugar content than the upward flux. Therefore, the larger diameter mist as downward flux is recirculated to the atomization chamber 1, the upward flux is bubbled into the water in the water tank 4, thus sugar and water in carrier gas is collected.

The water tank 4 has a role to collect water and sugar in the carrier gas. The collected separation water containing sugar is not thrown away and it is utilized as the saccharified solution. Therefore, as shown in FIG. 2, the separation water in the water tank 4 is supplied to the first tank 5 for the first saccharification step, or to the second tank 6 for the second saccharification step. By this method, the separation water separated from the saccharified solution in the first concentrating step is usefully reused for saccharification of biomass. According to the above method, the water cost for saccharification is reduced while biomass can be efficiently saccharified with plenty of water.

The saccharified solution concentrated in the first concentrating step, as shown in FIG. 1, is fermented to an alcohol water solution in the fermentation step, and the alcohol is purified to a higher concentration in the second concentrating step. The second concentrating step purifies the alcohol water solution to a high concentration of alcohol by both the atomization step to atomize the solution and the collection step.

The collection step can performs gathering and collection of the mist with aggregation. Additionally, the mist can be collected by adsorbing onto the molecular sieve adsorbent. The method employing the molecular sieve adsorbent can efficiently separate the high concentration alcohol according to separate the adsorption component as the water in mist onto the molecular sieve adsorbent from the non-adsorption component as the alcohol in mist. By this method, the alcohol water solution is atomized to mist into carrier gas. The water component (adsorption component) in the atomized mist is adsorbed onto the molecular sieve adsorbent. The mist separated by adsorbing water has high alcohol concentration. Under the condition, the non-adsorption component or high concentration alcohol is separated from the carrier gas. After next step, the alcohol component can be also adsorbed and collected by adsorbing onto another molecular sieve adsorbent from the mist containing high alcohol.

For example, when alcohol water solution is atomized to mist and the mist is collected, the alcohol concentration in the collected mist is higher than that in the not atomized residual solution. When a solution is atomized to mist and the mist is collected, the concentration of volatile substance or lower boiling point component in the collected mist is higher. The volatile and lower boiling point substances is atomized more easily to mist, and more easily vaporized from the surface of the mist, and the concentration in collected mist is higher than that in the original solution. Additionally, since the concentration in the surface of solution of substance having a property of surface excess is higher, when the solution located in the surface is atomized to mist, the concentration of substance having a property of surface excess is higher. Therefore, when the mist atomized from substance solution having a property of surface excess is collected, the concentration of the substance is higher. That is, the higher alcohol concentration can be separated from alcohol water solution. The separation device and the separation method to separate the high concentration alcohol from alcohol water solution are described as follows.

Figure 4:
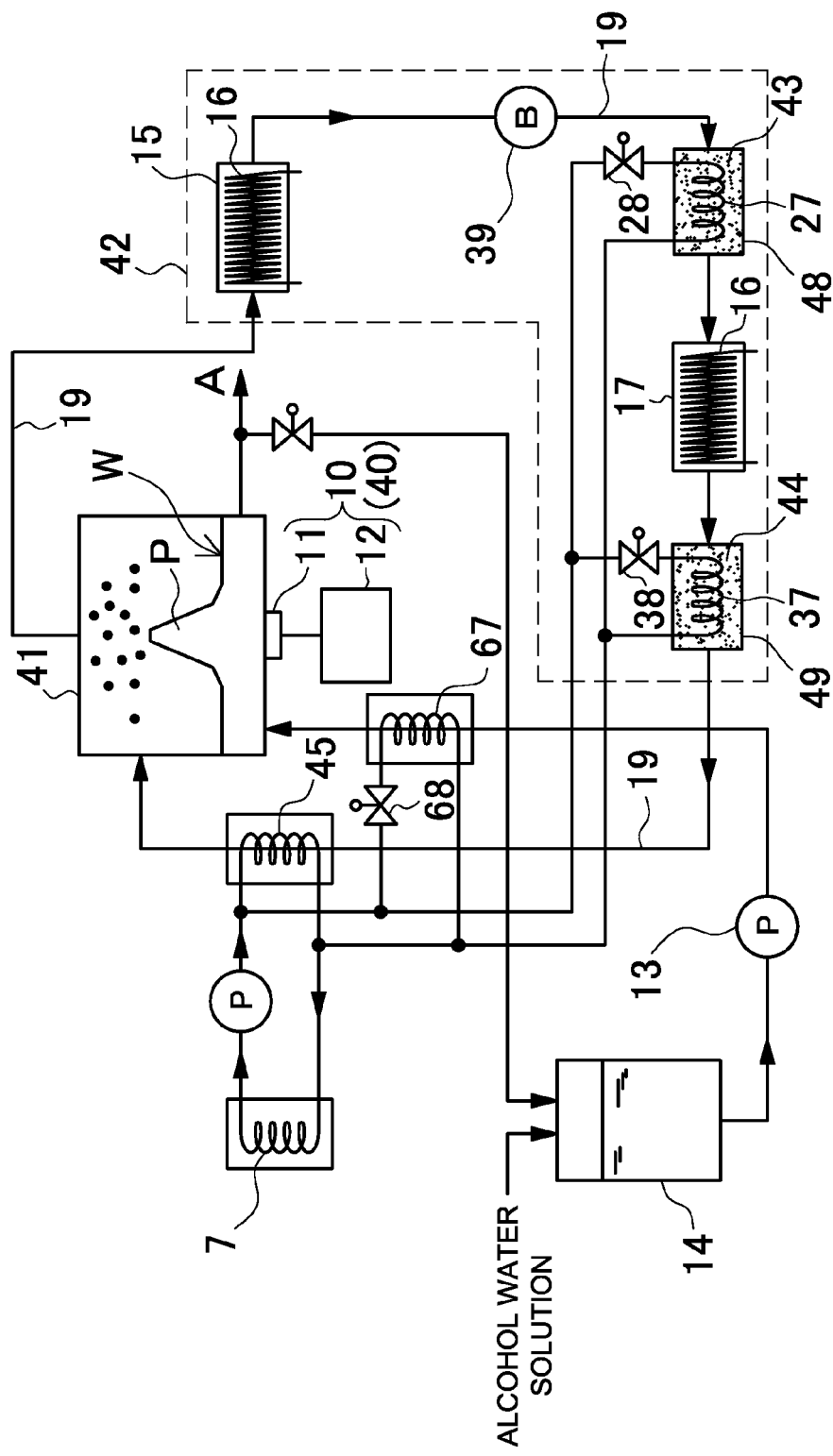
FIG. 4 is a schematic view showing a separation device for second concentrating step in the production method for biomass-alcohol according to an example of the present invention.

The separation device as shown in FIG. 4 includes the atomization chamber 41 to atomize the alcohol solution obtained in the fermentation step into the carrier gas, the atomization mechanism 40 to atomize the alcohol solution in the atomization chamber 41 into the carrier gas, the collection portion 42 to collect the mist atomized from alcohol water solution in the atomization mechanism 40, and the blower 39 to transfer the mist atomized in the atomization chamber 41 with the carrier gas.

According to the atomization method of alcohol water solution with ultrasonic vibration, the atomization efficiency is positively affected at higher temperature, because the amount of alcohol and water per a unit volume of air is increased when the carrier gas temperature is higher. In other words, the atomized mist amount per unit of ultrasonic vibration energy is increased. The separation device shown in the figure can maintain at the higher temperature condition with the thermal energy recovered from the heat exchangers where the saccharified solution in the first saccharification step is transferred to the first concentrating step. That is, the cooling heat exchanger 7 located with the transfer tube 9 for the saccharified solution transferred from a solid-liquid separator 73 for separating the saccharified slurry in the first saccharification step to the atomization chamber 1 in the first concentrating step is combinatorially used as the cooling heat exchanger to heat the carrier gas in the separation device in FIG. 4.

The separation device shown in FIG. 4 connects the cooling heat exchanger 7 to the heating heat exchanger 45 heating the carrier gas. The cooling heat exchanger 7 and the heating heat exchanger 45 circulate the coolant. The coolant temperature is elevated by absorbing the thermal energy of the saccharified solution in the cooling heat exchanger 7, the absorbed heat is released at the heating heat exchanger 45, and then the carrier gas is heated. As the coolant, water or oil can be also utilized. After this coolant absorbs the thermal energy of the saccharified solution obtained in the first saccharification step, the coolant adds the heat to the cooling heat exchanger 7, and the coolant is discharged. For example, the coolant is discharged from the cooling heat exchanger 7 at 45° C. The coolant heated and discharged in the cooling heat exchanger 7 heats the carrier gas to generate the mist in the heating heat exchanger 45. The carrier gas is heated in the heating heat exchanger 45, and supplied to the atomization chamber 41. The coolant temperature is decreased after the carrier gas is heated. The coolant decreased temperature is circulated from the heating heat exchanger 45 to the cooling heat exchanger 7, the coolant chills the cooling heat exchanger 7, and then chills again the saccharified solution obtained in the first saccharification step. That is, the coolant absorbs the thermal energy of the saccharified solution obtained in the first saccharification step, the adsorbed thermal energy heats the carrier gas. The heating heat exchanger 45 heats the carrier gas to 25-30° C. However, the heating heat exchanger 45 heats the carrier gas to 15-40° C., the heated carrier gas can be also supplied to the atomization chamber 41. According to rising of the temperature of the carrier gas supplied to the atomization chamber 41, the mist atomization rate is accelerated, however, alcohol will be changed its nature if excess rising of the temperature. On the other hand, temperature decreasing will cause the mist atomizing efficiency to be decreased.

Moreover, the cooling heat exchanger 7 can be used as the heating mean for alcohol water solution supplied to the atomization chamber 41. The method that the alcohol water solution is atomized by ultrasonic vibration is enhanced by temperature rising of alcohol water solution on atomization efficiency. If the solution temperature is maintained higher, the smaller ultrasound energy can efficiently atomize the solution to mist. As shown in FIG. 4, the separation device connects the cooling heat exchanger 7 with the heating heat exchanger 67 to heat the alcohol water solution supplied from a reservoir 14 to the atomization chamber 41, the coolant is circulated between the cooling heat exchanger 7 and the heating heat exchanger 67. The separation device in the FIG. 4 has the inlet valve 68 to control the coolant circulation at the inlet side of the heating heat exchanger 67. The alcohol water solution supplied from the reservoir 14 to the atomization chamber 41 is heated according to this separation device makes the coolant circulate to the heating heat exchanger 67 by opening the inlet valve 68. The heating heat exchanger 67 heats the alcohol water solution to 25-30° C. supplied to the atomization chamber 41. However, the heating heat exchanger 67 can also heat the alcohol water solution to 15-40° C. When the temperature of the alcohol water solution supplied to the atomization chamber 41 is raised at higher, the mist atomization efficiency is maintained at higher level. The excess raising of the temperature may cause the alcohol to be changed its nature. Therefore, the temperature set point of alcohol water solution by the heating heat exchanger 67 has to be optimum level considering with above reason.

Moreover, the cooling heat exchanger 7 as shown in FIG. 4 can be utilized for heating the adsorbent. This the cooling heat exchanger 7 is connected to the heating heat exchanger 27 and 37 to heat the adsorbent, the coolant within the heat exchangers is circulated. The heating heat exchanger 27 in FIG. 4 makes the adsorbed component obtained by heating the molecular sieve adsorbent 43 effectively discharge. Additionally, the heating heat exchanger 37 in FIG. 4 makes the non-adsorption component adsorbed on a second adsorbent 44 effectively discharge by heating the second adsorbent 44.

Figure 3:
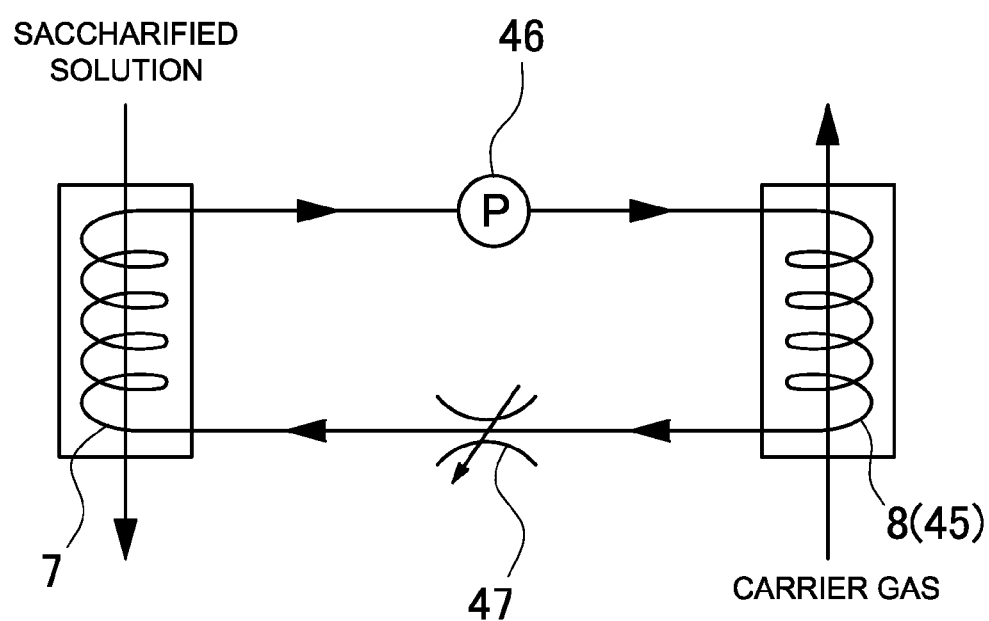
FIG. 3 is a schematic view showing the cooling heat exchanger and the heating heat exchanger according to another example of the present invention.

Moreover the coolant can cools the cooling heat exchanger by the own vaporization heat, and heats the heating heat exchanger by the own condensation heat. The cooling mechanism in order to cool and heat the heat exchanger with the vaporization heat of coolant and its condensation heat compresses the coolant at the compressor 46, and supplies to the heating heat exchanger 45 as same as describing at FIG. 3. The heating heat exchanger 45 discharges the heat of the coolant, liquefies the coolant, and heats by the condensation heat of the coolant. The liquefied coolant is supplies to the cooling heat exchanger 7 via an expansion valve 47. The expansion valve 47 makes the coolant adiabatic expansion, and vaporizes the coolant within the cooling heat exchanger 7. Therefore, the cooling heat exchanger 7 is cooled by the vaporization heat of the coolant. The vaporized coolant is transferred into the compressor 46, and circulated to the heating heat exchanger 45. This cooling mechanism can maintain the temperature of the heating heat exchanger 45 at higher level while the cooling heat exchanger 7 is cooled at lower temperature. Therefore, in the second concentrating step, the temperature of carrier gas supplied to the atomization chamber 41 can be maintained at high temperature. Additionally, although not shown, the cooling mechanism in order to cool and heat the heat exchangers utilizing the vaporization heat and the condensation heat by connecting the cooling heat exchanger to the heating heat exchanger to heat the adsorbent can heat the molecular sieve adsorbent at high temperature, discharge the adsorbed component, and quickly discharge non-adsorption component by heating the second adsorbent at high temperature.

The alcohol water solution is supplied from a reservoir 14 to the atomization chamber 41, and atomized into mist in the atomization mechanism 40. The atomization mechanism 40 atomizes some solutions into mist by ultrasonic vibration. The atomization mechanism 40 to atomize the alcohol water solution into mist by ultrasonic vibration is the ultrasonic atomization mechanism 10 the alcohol water solution in the atomization chamber 41 into mist by ultrasonic vibration. This ultrasonic atomization mechanism 10 includes one or plural ultrasonic oscillator to atomize the alcohol water solution into mist, and the ultrasonic power supply 12 to supply the high frequency electricity into the ultrasonic oscillator 11 and to make the ultrasonic oscillator 11 to ultrasonically oscillate. The separation device as shown in FIG. 4 is transferring the mist atomized from the alcohol water solution with the carrier gas to the collection portion 42 by a blower 39. It should be noted that, although not shown, a separation device may be also designed as the structure with mist transferring mechanism employing electrostatic mean or ultrasonic mean.

The atomization chamber 41 as shown in FIG. 4 can be continuously supplied the alcohol water solution from the reservoir 14 via a pump 13 connected to the reservoir 14 storing the alcohol water solution in the fermentation step. This separation device prevents the alcohol concentration of alcohol water solution in the atomization chamber 41 from decreasing by discharging the treated alcohol water solution in the atomization chamber 41 and supplying the new alcohol water solution from the reservoir 14. Additionally, as shown by arrow A in FIG. 4, the alcohol concentration of alcohol water solution in the reservoir 14 can be also prevented from decreasing by discharging the alcohol water solution in the atomization chamber 41 out of the reservoir 14. The alcohol water solution in the atomization chamber 1 can be renewed after the alcohol concentration of alcohol water solution decreased. In this method, the alcohol water solution is renewed at batch-wise.

The solution in the atomization chamber 41 is atomized into mist with an ultrasonic atomization mechanism 10. The mist atomized in the ultrasonic atomization mechanism 10 has higher concentration of target substance than concentration of target substance in the original solution before atomization. Therefore, the solution having high concentration of target substance can be efficiently separated by atomizing into mist from the original solution.

The alcohol water solution in the atomization chamber 41 is atomized by ultrasonically vibration of the ultrasonic atomization mechanism 10 into the mist having higher concentration ethanol the atomization chamber 41 than that in the original alcohol water solution from solution surface W. The liquid pillar P is formed on the liquid surface W when the alcohol water solution is ultrasonically vibrated. The mist is atomized from the surface of this pillar P. The ultrasonic atomization mechanism 10 is set on the bottom of the atomization chamber 41 reserving alcohol water solutions with facing up the surface of an ultrasonic oscillator 11 of the ultrasonic atomization mechanism 10. The ultrasonic oscillator 11 irradiates ultrasound from bottom toward the solution surface W, the irradiated solution surface W forms a liquid pillar P. The ultrasonic oscillator irradiates ultrasound vertically. The ultrasonic atomization mechanism that the plural ultrasonic oscillators ultrasonically vibrate the alcohol water solution can more efficiently atomize the alcohol water solution into mist.

Moreover, the bad influence can be solved by the ultrasonic oscillator 11 and the ultrasonic power supply is compulsory cooled. The ultrasonic oscillator 11 and the ultrasonic power supply can be cooled by, for example, cooling pipes is thermally connected to them. The cooling pipe running liquid or coolant tiled by cooler, ground water, or tap water can cool the ultrasonic oscillator 11 and the ultrasonic power supply.

The alcohol water solution mist atomized in the atomization chamber 41 is carried to the collection portion 42 by carrier gas. The collection portion 42 is connected with the atomization chamber 41 via a transfer duct 19 in order to carrier the mist into the collection portion 42. The separation device in FIG. 4 has a structure that the carrier gas is circulated between the collection portion 42 and the atomization chamber 41 with the blower 39. In the separation device, the carrier gas in the atomization chamber 41 is transported to the collection portion 42, separated from mist, and recirculated to the atomization chamber 41. In the separation device, hydrogen gas or helium gas is preferably filled as the carrier gas into the atomization chamber 41 and the collection portion 42. It is also preferable for the carrier gas that the mixed gas of hydrogen and helium, the mixed gas of hydrogen and air, the mixed gas of helium and air, or the mixed gas of hydrogen, helium and air. Moreover, inert gas as the carrier gas can be filled into the atomization chamber 41 and the collection portion 42.

Figure 5:
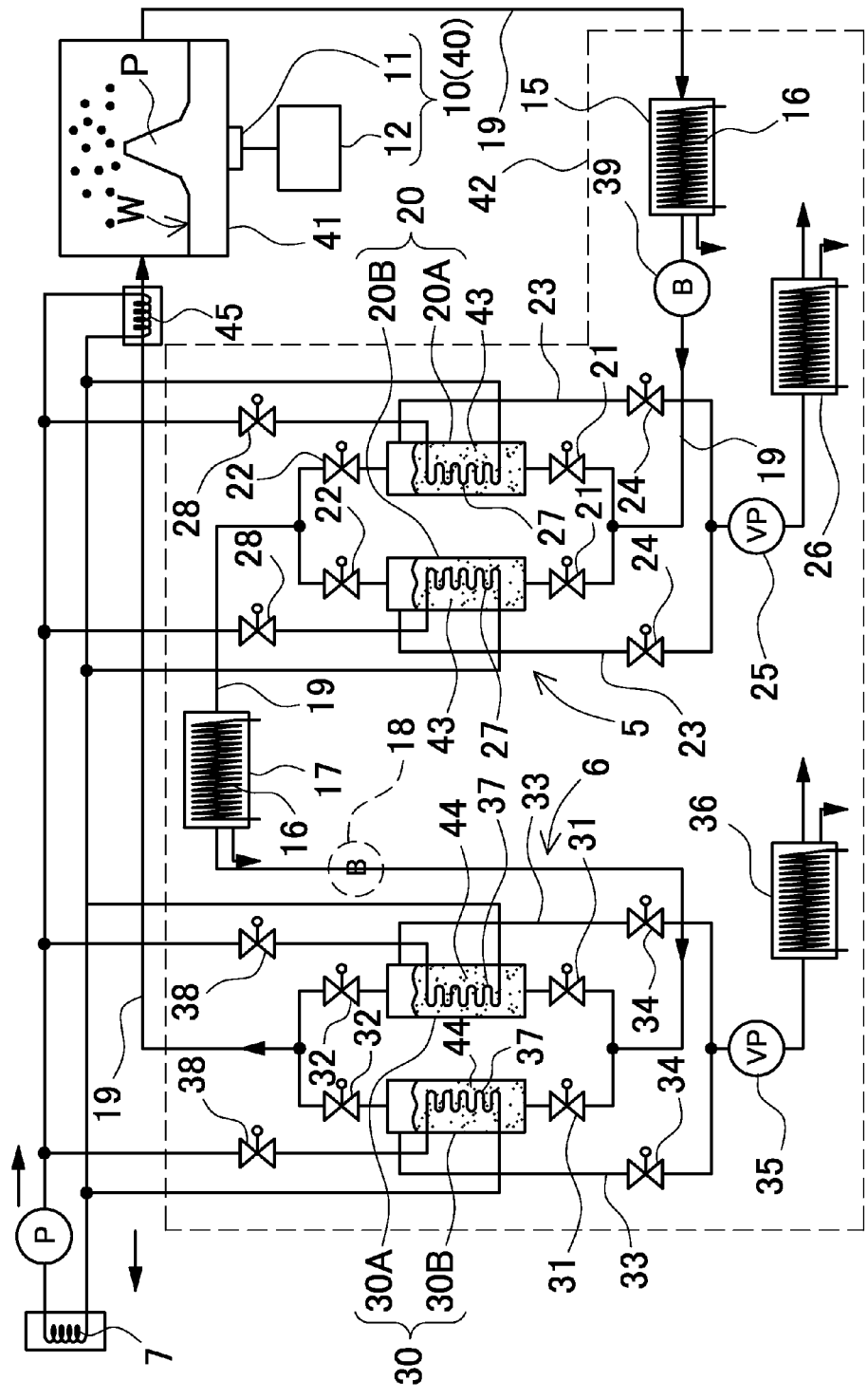
FIG. 5 is a schematic view showing a part of collection portion of the separation device showed in FIG. 4 according to an example of the present invention.
Figure 6:
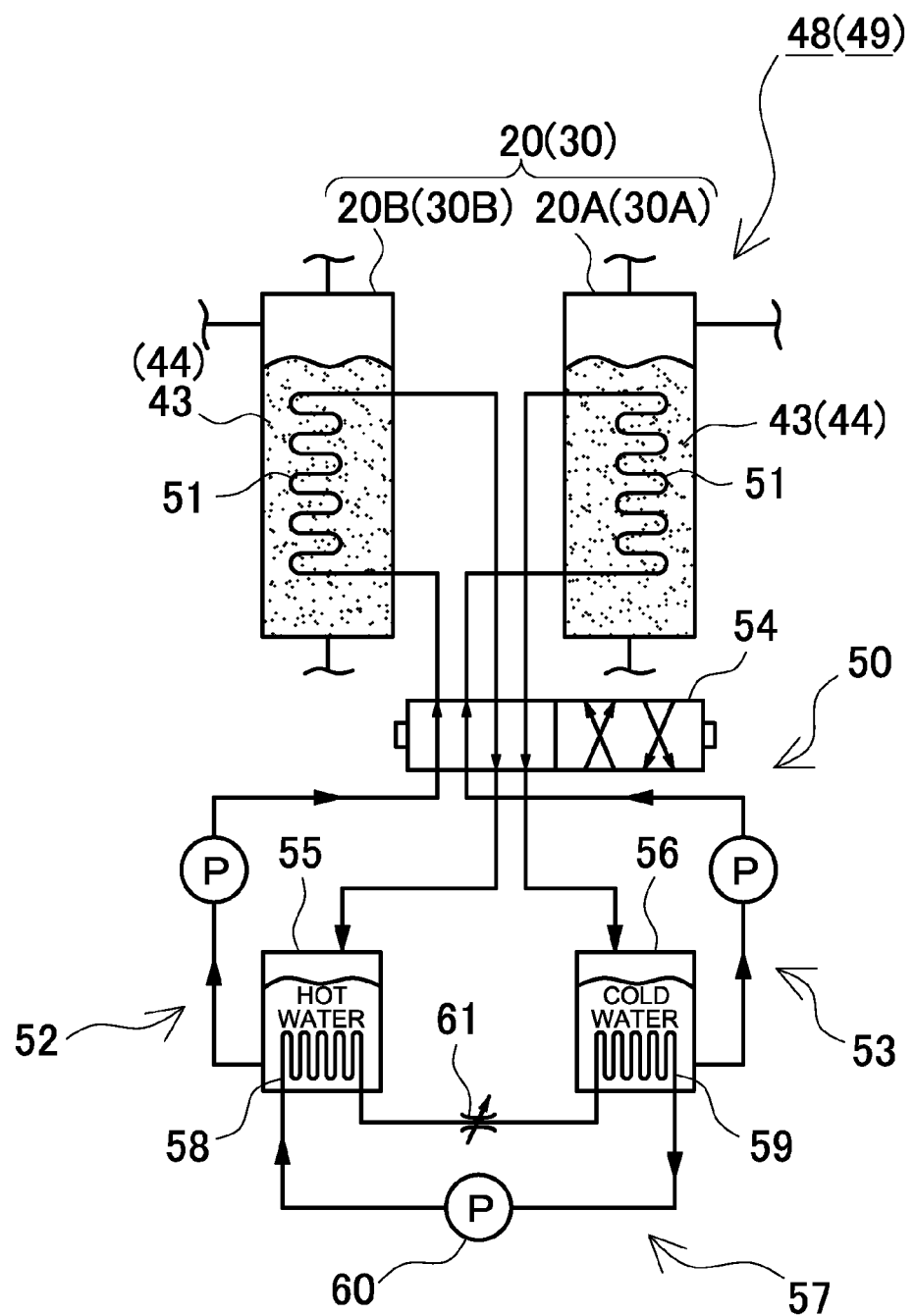
FIG. 6 is a schematic view showing temperature control portion according to an example of the present invention.

The collection portion 42 recovers the mist atomized at the atomization chamber 41 from carrier gas. The collection portion 42 shown in FIG. 4 and FIG. 5 is consisted from the adsorption collection portion 48 to recover the adsorption component in the mist from the carrier gas and the adsorption collection portion 49 to recover the non-adsorption component in the mist that is not adsorbed at the collection portion 48. Moreover, the collection portion 42 in FIG. is prepared the cooling portion 15 to cool the carrier gas supplied to the adsorption collection portion 48.

The adsorption efficiency on the adsorbent is elevated by cooling the carrier gas in the cooling portion 15. And, the cooling portion 15 recovers alcohol water solution with higher alcohol concentration collected from the mist in carrier gas atomized from the original alcohol water solution. The alcohol water solution recovered at the cooling portion 15 has higher alcoholic concentration than the original alcohol water solution before atomization, on the other hand, has lower alcoholic concentration than the alcohol concentration in the alcohol water solution recovered at the separation collection portion 49. For example, when the alcohol concentration in the original alcohol water solution is 40-80 wt. %, the alcohol concentration in the alcohol water solution recovered at cooling portion 15 is around 55 wt. % to 85 wt. %. The alcohol concentration in the alcohol water solution recovered at the separation collection portion 49 reaches more than 97 wt. % in the case of 40-80 wt. % of alcohol concentration in the original alcohol water solution, as mentioned as follows.

The cooling portion 15 shown in FIG. 5 is built in the cooling unit 16 to cool the carrier gas and the mist in the chamber with closed structure. The cooling unit 16 in the figure is the heat exchanger including heat exchanging pipes fixed with fins (not shown). This cooling unit 16 cools cooling water or coolant circulated in heat exchanging pipes. The cooling unit can be also consisted from electric cooling unit with Peltier devices. A part of the mist atomized in the atomization chamber 41 is condensed and aggregated in the cooling unit 16. The carrier gas containing mist cooled in the cooling portion 15 is transferred to the adsorption collection portion 48. The mist is not necessarily aggregated with cooling because the mist is not gas. However, it is just efficiently recovered by cooling.

The adsorption collection portion as shown in FIG. 5 separates the water content in the mist from the carrier gas cooled in the cooling portion 15 by adsorbing onto the molecular sieve adsorbent 43. The collection portion 48 separates the water content in the mist from the carrier gas by following two steps. The first step is the adsorption step to adsorb the water content in the mist as adsorption component onto the molecular sieve adsorbent 43, and the second step is the desorption step to discharge the water content adsorbed onto the molecular sieve adsorbent 43 in the first adsorption step from the molecular sieve adsorbent 43.

The pressure in desorption step is set lower than that in adsorption step, whereby the adsorption collection portion 48 separates the water content as adsorption component from the mist. Therefore, in the adsorption collection portion 48, the pressure in the case of desorbing the adsorbed adsorption component is set lower than that in the case of adsorbing the adsorption component, whereby the water content as the adsorption component is separated from the mist.

The reason why the pressure in the desorption step is lowered than that in the adsorption step is that the adsorption amount onto the molecular sieve adsorbent 43 is changed by the pressure around the molecular sieve adsorbent. The property that the molecular sieve adsorbent 43 adsorbs the water content as adsorption component depends on kinds of the molecular sieve adsorbent 43 and the varieties of the adsorption component, generally, the adsorption amount adsorbed onto adsorbent is elevated with the pressure increasing and decreased with the pressure decreasing under same temperature condition. Additionally, the adsorption amount onto the molecular sieve adsorbent 43 is lowered with temperature increasing and elevated with temperature decreasing under same pressure condition.

The adsorption collection portion 48 recovers the alcohol water solution with high alcohol concentration by separating the adsorption component in mist according to the above property. Therefore, in the adsorption step, the pressure in the desorption step is lowered than that in adsorption step whereby a large volume of adsorption component is adsorbed onto the molecular sieve adsorbent 43, in the desorption step, the amount of adsorption component onto the molecular sieve adsorbent 43 is restricted whereby the adsorption component adsorbed on is discharged from the molecular sieve adsorbent 43.

The adsorption collection portion 48 shown in FIG. 5 includes the seal chamber 20 filled the molecular sieve adsorbent 43, the open and close valve 21 and 22 to control the carrier gas passing into the seal chamber 20 or from the seal chamber 20, and the vacuum pump 25 connected to the seal chamber 20 to vacuum the seal chamber 20.

The seal chamber 20 has a closed chamber structure, and is filled with the molecular sieve adsorbent 43. The molecular sieve adsorbent 43 is a molecular sieve made from synthesized zeolite. The molecular sieve is utilized at valid pore size to adsorb water molecule as the adsorption component, for example, the valid pore size is 3 angstroms. The valid pore size of the molecular sieve adsorbent 43 is different at every adsorption component. For example, 5 angstroms molecular sieves adsorb normal paraffin with more than 3 carbons, on the other hand, do not adsorb iso-paraffin, benzene, toluene, while this 5 angstroms molecular sieves can separate normal paraffin with more than 3 carbons from iso-paraffin, benzene, toluene.

The seal chamber 20 is connected to outlet side of the cooling portion 15 via the transfer duct 19. The carrier gas including mist from the cooling portion 15 makes the molecular sieve adsorbent 43 adsorb the adsorption component through the seal chamber 20. The outlet side of the seal chamber 20 is connected to the separation collection portion 49 such that the carrier gas which absorbs water of the adsorption component is supplied to the separation collection portion 49.

Moreover, in FIG. 5, the outlet side of the seal chamber 20 is connected to the separation collection portion 49 via the transfer duct 19. The transfer duct 19 connected to the inlet side of the seal chamber 20 includes the open and close valve 21, the transfer duct 19 connected to the outlet side is set the open and close valve 22. In adsorption collection portion 48, under the condition that the carrier gas with mist is supplied to the seal chamber 20 at the open status of the open and close valve 21, mist in the carrier gas is adsorbed on the molecular sieve adsorbent 43.

Moreover, the seal chamber 20 is connected to the inlet side of the vacuum pump 25 via the aspiration duct 23. The aspiration duct is set the aspiration valve 24. The vacuum pump 25 forcibly exhausts from the seal chamber 20, the inner pressure in the seal chamber 20 is decreased. The molecular sieve adsorbent 43 discharges the adsorbed adsorption component under the pressure reduced. The vacuum pump 25 forcibly exhausts the adsorption component discharged from the molecular sieve adsorbent 43. In the device shown in FIG. 5, the outlet side of the vacuum pump 25 is connected to the cooling unit 26. The cooling unit 26 cools the adsorption component from the molecular sieve adsorbent 43, condenses or gathers into the collected liquid water. Therefore, the cooling unit 26 evacuates the water as the adsorption component adsorbed on the molecular sieve adsorbent 43. This cooling unit is not just necessarily used. The device that the adsorption component is water can abandon water as the adsorption component discharged from molecular sieve adsorbent.

The separation device shown in the figure set the blower 39 between the cooling portion 15 and the adsorption collection portion 48. This separation device supplies the carrier gas circulating by the blower 39 to the adsorption collection portion 48 and the separation collection portion 49 under the compressed pressure. For example, the blower 39 supplies the carrier gas compressed more than atmospheric pressure to the adsorption collection portion 48 and the separation collection portion 49. The separation device that supplies the carrier gas compressed to the adsorption collection portion 48 and the separation collection portion 49 can elevate the adsorption amount in the adsorption step, whereby the adsorption component and non-adsorption component can be efficiently separated from the carrier gas. The adsorption collection portion 48 can individually control the open and close valve 21 connected to the inlet side of the seal chamber 20 and open and close valve 22 connected to the outlet side of the seal chamber 20, whereby the pressure of the carrier gas supplied to the seal chamber 20 can be adjusted. Moreover, it is not necessarily to make the carrier gas pressure set over atmospheric pressure in the separation device, also set at atmospheric pressure.

Moreover, the adsorption collection portion 48 shown in FIG. 5 includes a first seal chamber 20A and a second seal chamber 20B as a pair of the seal chamber 20. This structured adsorption collection portion 48 mutually employs a pair of seal chamber 20 as an adsorption step or desorption step, the pair of seal chamber 20 can efficiently separate water as adsorption component. This structured adsorption collection portion 48 separates the adsorption component from the carrier gas as follows.

(1) The open and close valve 21, 22 in the first seal chamber 20A are opened, simultaneously the open and close valve 21, 22 in the second seal chamber 20B and the aspiration valve 24 in the first seal chamber 20A are closed. Under the above condition, the carrier gas supplied from the cooling portion 15 is flowed into the first seal chamber 20A, water as the adsorption component is adsorbed onto the molecular sieve adsorbent 43 filled in the first seal chamber 20A.

(2) After setting duration, the open and close valve 21, 22 in the first seal chamber 20A and the aspiration valve 24 in the second seal chamber 20B are closed, simultaneously the open and close valve 21, 22 in the second seal chamber 20B are opened. Under above condition, the carrier gas supplied from the cooling portion 15 is not flowed into the first seal chamber 20A, is flowed into the second seal chamber 20B. Water as the adsorption component is adsorbed onto the molecular sieve adsorbent 43 filled in the second seal chamber 20B.

(3) The aspiration valve 24 in the first seal chamber 20A is opened, a vacuum pump 25 exhausts from the first seal chamber 20A. The inner pressure of the first seal chamber 20A is reduced, whereby water as the adsorption component is separated from the molecular sieve adsorbent 43.

(4) Water as the adsorption component separated from the molecular sieve adsorbent 43 in the first seal chamber 20A is exhausted from the first seal chamber 20A, flowed into the cooling unit 26, cooled and condensed at the cooling unit 26, and aggregated and collected. The adsorption component is not necessarily cooled at the cooling unit, can also be exhausted out the device by vacuum pump.

(5) Moreover, after setting duration, the open and close valve 21, 22 in the first seal chamber 20A are opened, the open and close valve 21, 22 in the second seal chamber 20B and the aspiration valve 24 in the first seal chamber 20A are closed. Under the above condition, the carrier gas supplied from the cooling portion 15 is not flowed into the second seal chamber 20B, is flowed into the first seal chamber 20A. Water as the adsorption component is adsorbed onto the molecular sieve adsorbent 43 filled in the first seal chamber 20A.

(6) The aspiration valve 24 in the second seal chamber 20B is opened, the vacuum pump 25 exhausts from the second seal chamber 20B. The inner pressure of the second seal chamber 20B is reduced, whereby water as the adsorption component is separated from the molecular sieve adsorbent 43.

(7) Water as the adsorption component separated from the molecular sieve adsorbent 43 in the second seal chamber 20B is exhausted from the second seal chamber 20B, flowed into the cooling unit 26, cooled and condensed at the cooling unit 26, and aggregated and collected. The adsorption component is not also necessarily cooled at the cooling unit, can also be exhausted out the device by vacuum pump.

(8) By repeating step from (2) to (7), the open and close valve 21, 22 are mutually opened and closed, whereby the pair of the seal chamber 20 separates the adsorption component from mist.

Moreover, in the adsorption collection portion 48, the temperature of molecular sieve adsorbent 43 in adsorption step is set lower than the temperature of molecular sieve adsorbent 43 in desorption step, whereby the adsorption component in the carrier gas is more efficiently collected. Because the adsorption amount onto the molecular sieve adsorbent 43 is depended on temperature as mentioned above. For example, the adsorption collection portion 48 can elevate the adsorption amount by cooling the molecular sieve adsorbent 43 in the adsorption step. The collection portion 42 shown in the figure cools the carrier gas and mist at the cooling portion 15, and supplies into the adsorption collection portion 48. This separation device adsorbs much adsorption component in mist by cooling and elevating the adsorption amount in the adsorption step. It is not just necessarily for the collection portion 2 to set the cooling portion, to cool the carrier gas including mist. The not cooled carrier gas can be supplied into the adsorption collection portion.

Moreover, the adsorption collection portion 48 in desorption step can efficiently separate the adsorbed adsorption component by heating the molecular sieve adsorbent 43. Because the adsorption ability of the heated molecular sieve adsorbent 43 is decreased. The adsorption collection portion 48 shown in the figure. is set the heating heat exchanger 27 to heat the molecular sieve adsorbent 43 within each seal chamber 20. This heating heat exchanger 27 is connected into the cooling heat exchanger 7 at the concentrating device shown in FIG. 2. The heating heat exchanger 27 and the cooling heat exchanger 7 have a circulation structure of coolant. The coolant absorbs the thermal energy of the saccharified solution at the cooling heat exchanger 7, the temperature of coolant is increased, and the coolant discharges the heat absorbed at the heating heat exchanger 27 and heats the molecular sieve adsorbent 43. As the coolant, water or oil can be utilized. This coolant absorbs the thermal energy of the saccharified solution, the temperature of coolant is increased. Then the coolant is discharged from the cooling heat exchanger 7. The coolant heated and discharged from the cooling heat exchanger 7 the heats molecular sieve adsorbent 43 at the heating heat exchanger 27. The coolant temperature after heating the molecular sieve adsorbent 43 is decreased. The coolant after temperature down is circulated from the heating heat exchanger 27 to the cooling heat exchanger 7, the coolant cools the cooling heat exchanger 7, and cools again the saccharified solution obtained in the first saccharification step. Therefore, the coolant absorbs the thermal energy of the saccharified solution, the absorbed thermal energy heats the molecular sieve adsorbent 43.

The adsorption collection portion 48 in FIG. 5 separates water as the adsorption component by switching to the adsorption step and the desorption step in the pair of the seal chamber 20 including the first seal chamber 20A and the second seal chamber 20B. Therefore, the heating heat exchanger 27 set in each the seal chamber 20 heats the molecular sieve adsorbent 43 by circulation of the coolant, the adsorption component is quickly discharged non-adsorption component in the desorption step. The inlet sides of the heating heat exchangers 27 set in the first seal chamber 20A and the second seal chamber 20B of the adsorption collection portion 48 shown in the figure have inlet valve 28 to control the circulation of coolant. The inlet valve 28 in each seal chamber 20 is opened and closed in the desorption step, whereby the coolant is circulated to the heating heat exchanger 27, and heats the molecular sieve adsorbent 43.

The separation collection portion 49 collects the mist with high alcohol concentration consisted of the non-adsorption component after the adsorption collection portion 48 separates water as the adsorption component. The separation collection portion 49 separates the alcohol as non-adsorption component by adsorbing onto the second adsorbent 44. The separation collection portion 49 separates alcohol as the non-adsorption component from mist in the carrier gas with following two steps; adsorption step to adsorb alcohol in mist as the non-adsorption component onto the second adsorbent 44, and the desorption step to discharge alcohol as the non-adsorption component from the second adsorbent 44 that adsorbed alcohol in the adsorption step.

The pressure in the desorption step is lowered than that in the adsorption step, whereby the separation collection portion 49 separates alcohol as the non-adsorption component from mist as same in the adsorption collection portion 48.

The reason that the pressure in the desorption step is lowered that that in the adsorption step is because the adsorption amount onto the second adsorbent 44 is depended on the pressure in the seal chamber as same in the molecular sieve adsorbent 43. Additionally, the adsorption amount onto the second adsorbent 44 is decreasing with temperature increasing, on the other hand, is increasing with the temperature decreasing under the same pressure.

The second adsorbent 44 in the separation collection portion 49 collects alcohol containing higher concentration by adsorbing the non-adsorption component in mist. Therefore, the pressure in the desorption step is lowered than that in the adsorption step, whereby much non-adsorption component in the adsorption step is adsorbed onto the second adsorbent 44, and little non-adsorption component in the desorption step is adsorbed onto the second adsorbent 44, and the non-adsorption component can be discharged from the second adsorbent 44.

As the same as the above adsorption collection portion 48, the separation collection portion 49 includes the seal chamber 30 filled with the second adsorbent 44, the open and close valve 31, 32 to control the carrier gas flow passing into the seal chamber 30 or from the seal chamber 30, and the vacuum pump 35 connected to the seal chamber 30 to exhaust from the seal chamber 30.

The seal chamber 30 has a closed chamber structure, and is filled with the second adsorbent 44. The second adsorbent 44 is a molecular sieve made from synthesized zeolite to adsorb alcohol as non-adsorption component that can not be adsorbed onto the molecular sieve adsorbent 43. The second adsorbent 44 is utilized at valid pore size to adsorb alcohol as the non-adsorption component, for example, the valid pore size is 5 angstroms. As substances for the second adsorbent 44, every substance can be used for the mist separated by adsorption onto the molecular sieve adsorbent 43 is available, for example, zeolite, activated carbon, lithium oxide, silica gel, or these mixture.

The seal chamber 30 is connected to the outlet side of the adsorption collection portion 48 via the transfer duct 19. Moreover, in the separation device in the figure, the seal chamber 30 in the separation collection portion 49 is connected to the adsorption collection portion 48 via the cooling portion 17. The separation collection portion 49 separates alcohol as the non-adsorption component from the carrier gas cooled at the cooling portion 17 by adsorbing onto the second adsorbent 44. The chamber with a closed structure in the cooling portion 17 in the figure has the cooling unit 16 to cool the carrier gas and mist.

Moreover, in FIG. 5, the outlet side of the seal chamber 30 is connected to the atomization chamber 41 via the transfer duct 19. The transfer duct 19 connected to the inlet side of the seal chamber 30 has the open and close valve 31, transfer duct 19 connected to the outlet side is set the open and close valve 32. In the separation collection portion 49, under the condition that the carrier gas with mist is supplied to the seal chamber 30 at the open status of the open and close valve 31, the non-adsorption component in mist in the carrier gas is adsorbed on the molecular sieve adsorbent 43.

Moreover, the seal chamber 30 is connected to the inlet side of the vacuum pump 35 via the aspiration duct 33. The aspiration duct 33 is set the aspiration valve 34. The vacuum pump 35 forcibly exhausts from the seal chamber 30, the inner pressure in seal chamber 30 is decreased. The second adsorbent 44 discharges the adsorbed non-adsorption component under the pressure reduced. The vacuum pump 35 forcibly exhausts the non-adsorption component discharged from the second adsorbent 44. In the device shown in the figure, the outlet side of the vacuum pump 35 is connected to the cooling unit 36.

The cooling unit 36 cools the non-adsorption component from the second adsorbent 44, condenses or gathers into the collected alcohol solution with high concentration. Therefore, the cooling unit 36 evacuates alcohol with high concentration as the non-adsorption component adsorbed onto the second adsorbent 44.

The separation device as shown by dotted line in FIG. 5 set the blower 18 between the adsorption collection portion 48 and the separation collection portion 49. The blower 18 compresses the carrier gas exhausted from the adsorption collection portion 48, and supplies the compressed carrier gas into the separation collection portion 49. For example, the blower 18 supplies the compressed carrier gas into the separation collection portion 49, whereby the adsorption amount of non-adsorption component in adsorption step can be elevated. It is not necessarily for the separation device to set the blower between the adsorption collection portion and the separation collection portion.

Moreover, the adsorption collection portion 49 shown in FIG. 5 includes first seal chamber 30A and second seal chamber 30B as a pair of the seal chamber 30, as same in the adsorption collection portion 48. This structured adsorption collection portion 49 mutually uses a pair of the seal chamber 30 as adsorption step or desorption step, the pair of the seal chamber 30 can efficiently separate alcohol as the non-adsorption component. This structured adsorption collection portion 49 separates the non-adsorption component from the carrier gas as follows.

(1) The open and close valve 31, 32 in the first seal chamber 30A are opened, simultaneously the open and close valve 31, 32 in the second seal chamber 30B and the aspiration valve 34 in the first seal chamber 30A are closed. Under the above condition, the carrier gas supplied from the adsorption collection portion 48 is flowed into the first seal chamber 30A, alcohol as the non-adsorption component is adsorbed onto the second adsorbent 44 filled in the first seal chamber 30A.

(2) After setting duration, the open and close valve 31, 32 in the first seal chamber 30A and the aspiration valve 34 in the second seal chamber 30B are closed, simultaneously the open and close valve 31, 32 in the second seal chamber 30B are opened. Under above condition, the carrier gas supplied from the adsorption collection portion 48 is not flowed into the first seal chamber 30A, is flowed into the second seal chamber 30B, while alcohol as the non-adsorption component is adsorbed onto the second adsorbent 44 filled in the second seal chamber 30B.

(3) The aspiration valve 34 in the first seal chamber 30A is opened, the vacuum pump 35 exhausts from the first seal chamber 30A. The inner pressure of the first seal chamber 30A is reduced, whereby alcohol as the non-adsorption component is separated from the molecular sieve adsorbent 44.

(4) Alcohol as the non-adsorption component separated from the second adsorbent 44 in the first seal chamber 30A is exhausted from the first seal chamber 30A, flowed into the cooling unit 36, cooled and condensed at the cooling unit 36, and aggregated and collected as high concentration alcohol.

(5) Moreover, after setting duration, the open and close valve 31, 32 in the first seal chamber 30A are opened, the open and close valve 31, 32 in the second seal chamber 30B and the aspiration valve 34 in the first seal chamber 30A are closed. Under the above condition, the carrier gas supplied from the adsorption collection portion 48 is not flowed into the second seal chamber 30B, is flowed into the first seal chamber 30A. Alcohol as the non adsorption component is adsorbed onto the second adsorbent 44 filled in the first seal chamber 30A.

(6) The aspiration valve 34 in the second seal chamber 30B is opened, the vacuum pump 35 exhausts from the second seal chamber 30B. The inner pressure of the second seal chamber 30B is reduced, whereby alcohol as the non-adsorption component is separated from the second adsorbent 44 into the alcohol solution containing high concentration alcohol.

(7) Alcohol as the non-adsorption component separated from the second adsorbent 44 in the second seal chamber 30B is exhausted from the second seal chamber 30B, flowed into the cooling unit 36, cooled and condensed at the cooling unit 36, and aggregated and collected.

(8) By repeating step from (2) to (7), the open and close valve 31, 32 are mutually opened and closed, whereby the pair of the seal chamber 30 separates high concentration alcohol as the non-adsorption component from mist.

Moreover, in the adsorption collection portion 49, the temperature of second adsorbent 44 in adsorption step is set lower than the temperature of the second adsorbent 44 in desorption step, whereby the non-adsorption component in the carrier gas is more efficiently collected. The collection portion 42 in FIG. 4 and FIG. 5 cools the carrier gas and mist at the cooling portion 17, and supplies into the adsorption collection portion 49. This separation device adsorbs more non-adsorption component in mist by cooling and elevating the adsorption amount of non-adsorption component in the second concentrating step. It is not just necessarily for the collection portion to set the cooling portion, to cool the carrier gas including mist. The not cooled carrier gas can be supplied into the separation collection portion.

Moreover, the adsorption collection portion 49 in desorption step can efficiently separate the adsorbed non-adsorption component by heating the second adsorbent 44, as same in the adsorption collection portion 48. Because the adsorption ability of the second adsorbent 44 heated is decreased. The adsorption collection portion 49 shown in the figure is set the heating heat exchanger 37 to heat the second adsorbent 44 within each seal chamber 30. This heating heat exchanger 37 is also connected into the cooling heat exchanger 7 at the concentrating device shown in FIG. 2. The heating heat exchanger 37 and the cooling heat exchanger 7 have a circulation structure of coolant. The coolant absorbs the thermal energy of the saccharified solution at the cooling heat exchanger 7, the temperature of coolant is increased, and the coolant discharges the heat absorbed at the heating heat exchanger 37 and heats the second adsorbent 44. As the coolant, water or oil can be utilized. This coolant absorbs the thermal energy of the saccharified solution, the temperature of coolant is increased. Then the coolant is discharged from the cooling heat exchanger 7. The coolant heated and discharged from the cooling heat exchanger 7 heats the second adsorbent 44 at the heating heat exchanger 37. The coolant temperature after the heat exchange with the second adsorbent 44 is decreased. The coolant with lower temperature is circulated from the heating heat exchanger 37 to the cooling heat exchanger 7, the coolant cools the cooling heat exchanger 7, and cools again the saccharified solution obtained in the first saccharification step. Therefore, the coolant absorbs the thermal energy of the saccharified solution, the absorbed thermal energy heats the second adsorbent 44.

The adsorption collection portion 49 in FIG. 5 separates alcohol as the non-adsorption component by switching to the adsorption step and the desorption step in the pair of the seal chamber 30 including the first seal chamber 30A and the second seal chamber 30B. Therefore, the heating heat exchanger 37 set in each the seal chamber 30 heats the second adsorbent 44 by circulation of the coolant, the adsorption component is quickly discharged the non-adsorption component in the desorption step. The inlet sides of the heating heat exchangers 37 set in the first seal chamber 30A and the second seal chamber 30B of the adsorption collection portion 49 in the figure have an inlet valve 38 to control the circulation of coolant. The inlet valve 38 in each seal chamber 30 is opened and closed in the desorption step, whereby the coolant is circulated to the heating heat exchanger 37, and heats the second adsorbent 44.

Moreover, the separation collection portion 49 to heat the second adsorbent 44 heats the carrier gas circulating from the separation collection portion 49 to the atomization chamber 41, whereby mist is efficiently atomized in the atomization chamber 41.

As mentioned above, the collection portion 42 cools the carrier gas transferred from the atomization chamber 41 to the adsorption collection portion 48 at the cooling portion 15. In the adsorption collection portion 48, the coolant circulated into the heating heat exchanger 27 connected to the cooling heat exchanger 7 in the concentrating device 40 heats the molecular sieve adsorbent 43. The adsorption collection portion 48 makes the carrier gas cooled at the cooling portion 15 adsorb onto the molecular sieve adsorbent 43, whereby, in the adsorption step, more adsorption component is adsorbed onto the molecular sieve adsorbent 43 by cooling the molecular sieve adsorbent 43, in the desorption step, the adsorption component is discharged from the molecular sieve adsorbent 43, because the adsorption ability of the adsorption component onto the molecular sieve adsorbent 43 is decreased by heating the molecular sieve adsorbent 43 with coolant circulated into the heating heat exchanger 27.

Similarly, in the separation collection portion 49, the carrier gas transferred from the adsorption collection portion 48 to the separation collection portion 49 is cooled at the cooling portion 17, the coolant circulated into the heating heat exchanger 37 connected to the cooling heat exchanger 7 in the concentrating device heats the second adsorbent 44. The adsorption collection portion 49 makes the carrier gas cooled at the cooling portion 17 adsorb onto the second adsorbent 44, whereby, in the adsorption step, more non-adsorption component is adsorbed onto the second adsorbent 44 by cooling the second adsorbent 44, in the desorption step, the non-adsorption component is discharged from the second adsorbent 44, because the adsorption ability of the non-adsorption component onto the second adsorbent 44 is decreased by heating the molecular sieve adsorbent 44 with coolant circulated into the heating heat exchanger 37.

Therefore, the collection portion 42 mentioned above cools the carrier gas transferred to the adsorption collection portion 48 and the separation collection portion 49 at the cooling portion 15, 17, respectively, whereby the collection portion 42 also cools the molecular sieve adsorbent 43 and the second adsorbent 44 in the adsorption step. The collection portion 42 heats the molecular sieve adsorbent 43 and the second adsorbent 44 at the heating heat exchanger 27, 37, respectively, whereby the collection portion 42 also heats the molecular sieve adsorbent 43 and the second adsorbent 44 in the desorption step. This structure can efficiently heat the adsorbent with the thermal energy recovered from the saccharified solution obtained in the first saccharification step. It is not just necessarily for the separation device to utilize the thermal energy obtained in the first saccharification step for the adsorbent heating. The separation device can also collect alcohol without heating the adsorbent. The separation device that separates the adsorption component at the molecular sieve adsorbent and separates the non-adsorption component at the second adsorbent can be efficiently operated by cooling the adsorbent in the adsorption step and heating the adsorbent in the desorption step. For example, the separation device can also control the temperature of the adsorbent with the temperature control portion 50 shown in FIG. 6.

The adsorption collection portion 48 shown in FIG. 6 has the temperature control portion 50 in order to control the temperature of the molecular sieve adsorbent 43 filled in the seal chamber 20. Moreover, similarly the separation collection portion 49 can control the temperature of the second adsorbent 44 filled in the seal chamber 30 with the temperature control portion 50.

The temperature control portion 50 has a structure that the molecular sieve adsorbent 43 filled in the seal chamber 20 can be cooled and heated. The temperature control portion 50 shown in the figure includes the heat exchanger 51 set in each seal chamber 20, the heating mechanism 52 to circulate the hot water into the heat exchanger 51 in the one seal chamber 20, the cooling mechanism 53 to circulate the cold water into the opposite seal chamber 20, the control valve 54 to switch the circulation of hot water or cold water into each seal chamber 20, and the cooling cycle 57 to heat the hot water tank 55 in the heating mechanism 52 and simultaneously to cool the cool water tank 56 in the cooling mechanism 53.

The heat exchanger 51 is set within the seal chamber 20. The heat exchanger 51 heats the molecular sieve adsorbent 43 in the state of hot water circulation, and cools the molecular sieve adsorbent 43 in the state of cold water circulation. The heating mechanism 52 has the heat radiator 58 of the cooling cycle 57 within the hot water tank 55, the seal chamber 20 is heated by the hot water heated at the heat radiator 58 circulating to circulation line. The cooling mechanism 53 has the heat absorber 59 of the cooling cycle 57 within the cool water tank 56, the seal chamber 20 is cooled by the cold water cooled at the heat absorber 59 circulating to circulation line. The heating mechanism and the cooling mechanism can be also circulated coolant except for water.

The cooling cycle 57 includes the compressor 60 to compress the evaporated coolant, the heat radiator 58 to condense the coolant compressed at the compressor 60, the heat absorber 59 to forcibly cool by the vaporization heat of the liquefied coolant, and the expansion valve 61 connected between the heat radiator 58 and the heat absorber 59. The expansion valve 61 makes the coolant liquefied by compression and cooling adiabatically expand within the heat absorber 59, whereby the heat absorber 59 is forcibly cooled by the vaporization heat of the coolant. The cooling cycle 57 adjusts the output of the compressor 60 and the divergence of the expansion valve 61 in order to control the temperature of the heat radiator 58 and the heat absorber 59 to the set temperature.

The temperature control portion 50 mentioned above heats by circulating the hot water into the heat exchanger 51 of the one seal chamber 20, and cools by circulating the cold water into the heat exchanger 51 of the opposite seal chamber 20, switching the control valve 54. Since the temperature control portion 50 with above structure can control heating and cooling of a pair of the seal chamber 20 by only one cooling cycle 57, the temperature in the molecular sieve adsorbent 43 filled in a pair of the seal chamber 20 can be efficiently controlled. In the adsorption collection portion 48 with a pair of the seal chamber 20, when the one seal chamber is held on a state of the adsorption step, the opposite seal chamber 20 is held on a state of the desorption step. Therefore, the temperature control portion 50 can efficiently adsorb the adsorption component onto the molecular sieve adsorbent 43 by cooling the seal chamber 20 in the adsorption step, simultaneously can efficiently separate the adsorption component adsorbed onto the molecular sieve adsorbent 43 by heating the seal chamber 20 in the desorption step.

Moreover, the heat radiator set within the hot water tank of the heating mechanism is connected with the cooling heat exchanger of the concentrating device, whereby the temperature control portion 50 not shown in the figure can also heat the hot water in the hot water tank by effectively utilizing the thermal energy recovered in the saccharification step

THE INDUSTRIAL APPLICABILITY

In the production method for biomass-alcohol according to the invention, biomass which is plants including polysaccharide such as cane, animals and/or waste organic materials is fermented, the highly concentrated alcohol that can not be produced by only fermentation can be produced from the fermented solution, the produced alcohol can be utilized for various uses such as fuel.

The invention claimed is:

1. A method for producing alcohol from biomass, the method comprising:
 a saccharification step of saccharifying biomass to produce a saccharified solution;
 a first concentrating step of ultrasonically vibrating the saccharified solution and atomizing the saccharified solution into a mist that is carried by a carrier gas, so as to elevate the sugar concentration in the saccharified solution by removing water from the saccharified solution;
 a fermentation step of fermenting the saccharified solution concentrated in the first concentrating step to form an alcohol water solution; and
 a second concentrating step of separating alcohol from the alcohol water solution fermented in the fermentation step,
 wherein the saccharification step includes a first saccharification step wherein the biomass is saccharified by an acid and a second saccharification step wherein the biomass is saccharified by an enzyme under a lower temperature than the temperature of the first saccharification step, thermal energy is recovered through cooling the saccharified solution at the first saccharification step and simultaneously the carrier gas in the first concentrating step is heated by the recovered thermal energy, and the saccharified solution is ultrasonically atomized into a mist carried by the carrier gas heated by the recovered energy, and
 wherein the thermal energy which is recovered in the saccharification step is utilized for heating the carrier gas, the carrier gas being supplied to an atomization chamber where the saccharified solution is ultrasonically atomized in the carrier gas to be concentrated in the first concentrating step, and wherein thermal energy recovered at the first saccharification step or the second concentrating step is utilized for heating the saccharified solution in the first concentrating step.

2. The method for producing alcohol from biomass according to claim 1,
 wherein, in the first concentrating step, part of the mist atomized from the saccharified solution is further passed into liquid water, and the liquid water including the atomized mist is used in the saccharification step for biomass saccharification.

3. The method for producing alcohol from biomass according to claim 1, wherein the mist atomized by ultrasonic vibration is separated by a cyclone, and a downward flux separated in the cyclone is circulated to the saccharified solution.

4. The method for producing alcohol from biomass according to claim 1, wherein, the mist atomized by ultrasonic vibration in the first concentrating step is separated by a cyclone, an upward flux separated in the cyclone is liquefied by bubbling in water bulk, and the liquefied water is utilized for saccharification of biomass in the saccharification step.

5. The method for producing alcohol from biomass according to claim 1, wherein the saccharification step further comprises:
 a first saccharification step of saccharifying hemicellulose in biomass by acid; and
 a second saccharification step of saccharifying cellulose in biomass by enzyme.

6. The method for producing alcohol from biomass according to claim 5, wherein hemicellulose in biomass is saccharified by acid and heat in the first saccharification step.

7. The method for producing alcohol from biomass according to claim 6, wherein hemicellulose in biomass is saccharified by acid and heat under the thermal condition between 140° C. and 200° C. in the first saccharification step.

8. The method for producing alcohol from biomass according to claim 5, wherein, after cooling of saccharified solution slurry saccharified in the first saccharification step, the slurry is separated to saccharified solution and solid content, the separated saccharified solution is transferred to the first concentrating step, and the separated solid content is transferred to the second saccharification step and saccharified by enzyme.

9. The method for producing alcohol from biomass according to claim 1, wherein a surfactant is added to saccharified solution of biomass and atomized into mist in the first concentrating step.

10. The method for producing alcohol from biomass according to claim 1, wherein mist is collected under lower pressure condition than atmospheric pressure in the first concentrating step.

11. The method for producing alcohol from biomass according to claim 1, wherein atomized mist is carried by carrier gas containing hydrogen or helium or methane and collected in the first concentrating step.

12. The method for producing alcohol from biomass according to claim 1, wherein the saccharified solution heated in the saccharification step is atomized into mist in the first concentrating step.

13. The method for producing alcohol from biomass according to claim 1, wherein, biomass to be saccharified is fall into one or more of following items, wood chip, cane, corn, wheat, sea weed, organic waste.

14. The method for producing alcohol from biomass according to claim 1, wherein thermal energy recovered at the first saccharification step or the second concentrating step heats the carrier gas in the first concentrating step.

15. The method for producing alcohol from biomass according to claim 1, wherein the thermal energy which is recovered in the saccharification step is also utilized for heating the alcohol water solution in the second concentrating step, the heated alcohol water solution being ultrasonically atomized to separate the alcohol.

* * * * *